United States Patent [19]

Kauphusman et al.

[11] Patent Number: 4,781,185
[45] Date of Patent: Nov. 1, 1988

[54] CONNECTING APPARATUS FOR CATHETER ASSEMBLY

[75] Inventors: James V. Kauphusman, Champlin; Bruce H. Neilson, Brooklyn Park, both of Minn.

[73] Assignee: GV Medical, Inc., Minneapolis, Minn.

[21] Appl. No.: 887,196

[22] Filed: Jul. 21, 1986

[51] Int. Cl.⁴ ............................................. A61B 17/36
[52] U.S. Cl. .................. 128/303.1; 128/395; 604/95
[58] Field of Search ............ 128/303.1, 0.15, 395-398, 128/4-8, 656-658, 348.1, 344; 350/96.15, 0.2-0.6; 604/95, 280, 96-103; 219/121 L, 121 LA

[56] References Cited

U.S. PATENT DOCUMENTS

| | | |
|---|---|---|
| 3,396,727 | 8/1968 | Mount . |
| 3,890,970 | 7/1975 | Gullen . |
| 4,161,949 | 7/1979 | Thahawalla . |
| 4,256,106 | 3/1981 | Shoor . |
| 4,323,065 | 4/1982 | Kling . |
| 4,526,170 | 7/1985 | Tanner ............................. 128/303.1 |
| 4,538,609 | 9/1985 | Takenaka et al. ............... 128/395 X |
| 4,616,648 | 10/1986 | Simpson ................................. 604/95 |
| 4,650,467 | 3/1987 | Bonello et al. ........................ 604/95 |
| 4,658,817 | 4/1987 | Hardy ............................... 128/395 X |
| 4,669,465 | 6/1987 | Moore et al. ..................... 128/303.1 |

Primary Examiner—Kyle L. Howell
Assistant Examiner—Angela D. Sykes
Attorney, Agent, or Firm—Orrin M. Haugen; Thomas J. Nikolai; Frederick W. Niebuhn

[57] ABSTRACT

A manifold connector, sheath connector and housing connector are provided for independently connecting a fiber enclosing sheath and (laser enhanced) fiber optic catheter housing to a transluminal balloon catheter manifold. The housing connector includes a locking plate enclosure, and a planar locking plate contained in the enclosure to reciprocate between open and locking positions, and spring biased into the locking position. The sheath connector includes an elongate cylindrical body attached to the distal end of the sheath, a disc extended radially outward of the body, and a sleeve extended forwardly of the disc perimeter and coaxial with the body. Two elongate levers also are mounted to the disc perimeter, and normally are aligned with the sleeve. A detent extends radially inward from the distal end of each lever. The manifold connector has an annular groove formed in its exterior, which is positionable to receive a locking blade portion of the locking plate, thus to form an interlocking engagement of the housing connector and manifold connector. An annular recess, formed in the manifold connector behind the annular groove, receives and retains the detents when the sheath connector and manifold connector are engaged.

18 Claims, 3 Drawing Sheets

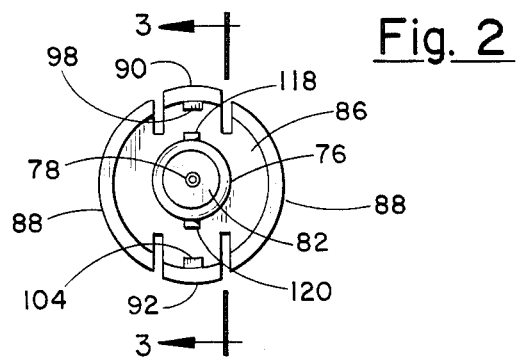
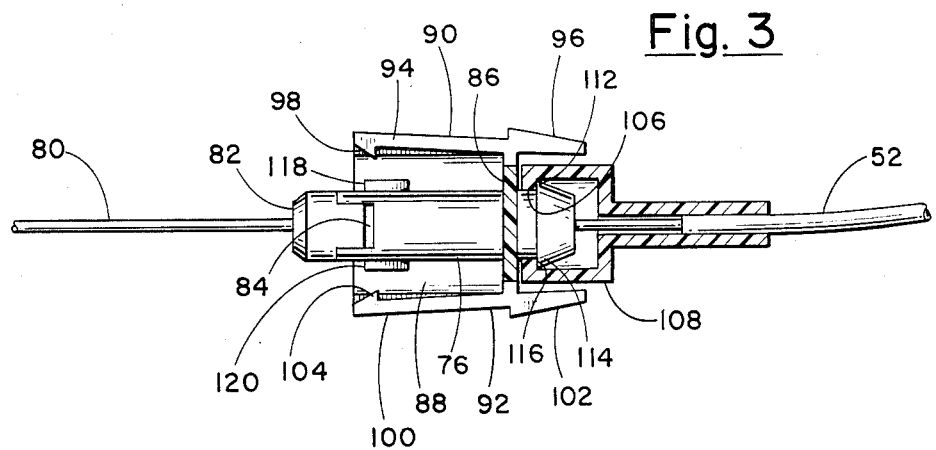
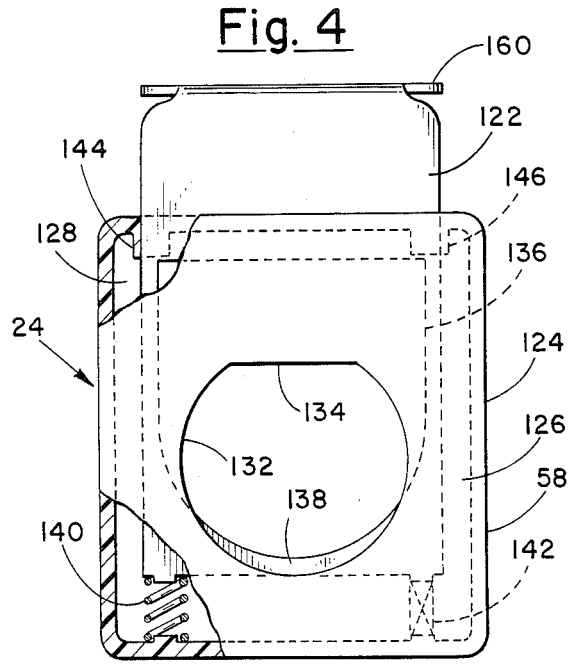
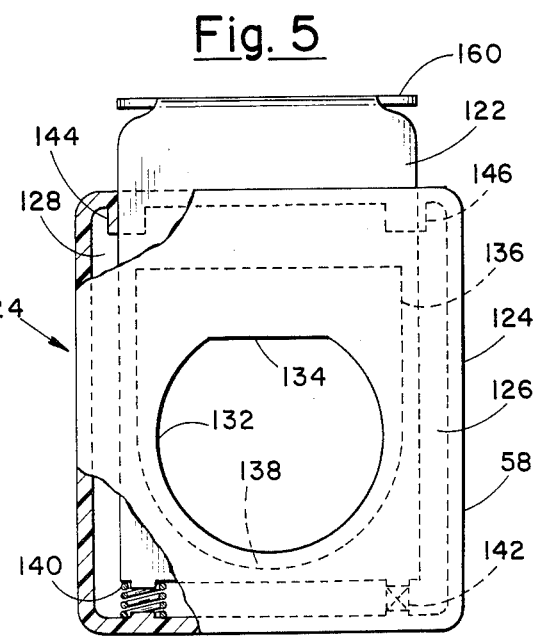

CONNECTING APPARATUS FOR CATHETER ASSEMBLY

BACKGROUND OF THE INVENTION

The present invention relates to laser transluminal angioplasty catheter assemblies and particularly to apparatus for releasably connecting the constituent parts of such assemblies.

Angioplasty catheter devices have been found useful in treating occlusions formed in blood vessels, for example from plaque build-up. In a laser enhanced catheter, an optical fiber is used to transmit a beam of laser energy from a generator to the fiber distal end, where the laser energy is delivered to and against the obstruction. Also, medication is delivered to the treatment area through one or more lumens in the catheter. Under controlled medication and exposure to the laser energy, the obstruction is partially removed, reduced in size, or eliminated entirely, effectively re-opening the blood vessel to restore normal circulation.

One known device for this technique is constructed by joining the proximal end of a catheter to a catheter manifold comprised of a plurality of luers, one for controlling inflation of a balloon at the catheter distal tip, and others for supplying treatment fluids at the catheter distal tip lumen. Further, a (laser enhanced) fiber optic catheter housing is releasably connected to the balloon catheter manifold, for supplying an optical fiber to the catheter system and controlling its advance within the catheter system. A final component of the device is a sheath enclosing part of the optical fiber and releasably connectable to the balloon catheter manifold independently of the (laser enhanced) fiber optic catheter housing. A substantially rigid fiber insertion tube, mounted distally with respect to the sheath, aids insertion of the optical fiber into the balloon catheter manifold.

Such device is disclosed in U.S. Pat. No. 4,669,465, assigned to the assignee of the present application. Typically, the fiber insertion tube is loaded into the manifold once the catheter has been inserted into a blood vessel requiring treatment. The sheath then is drawn rearwardly through the (laser enhanced) fiber optic catheter housing, in effect advancing the housing along the sheath toward the balloon catheter manifold. Simultaneously the optical fiber is advanced into and through the balloon catheter, until the housing contacts the balloon catheter manifold and is connected thereto. At this point, the location of the optical fiber relative to the balloon catheter can be controlled by manipulating a slide mounted on the (laser enhanced) fiber optic catheter housing.

The sheath/manifold connection and the housing/manifold connection both must be accomplished during the laser angioplasty procedure. Therefore, it is an object of the present invention to provide a means for rapidly effecting these required connections.

Another object is to provide a positive connecting means for substantially integrally joining a balloon catheter manifold with a (laser enhanced) fiber optic catheter housing.

Yet another object is to provide a connecting means which angularly aligns the catheter manifold and fiber advance housing during joinder, and ensures that only a properly matched optical fiber sheath can be connected to a particular catheter manifold.

SUMMARY OF THE INVENTION

To achieve these and other objects, there is provided an apparatus for releasably connecting the proximal end of a transluminal balloon catheter with respect to a (laser enhanced) fiber optic catheter housing. The apparatus includes a locking plate enclosure mounted at the distal end of a (laser enhanced) fiber optic catheter housing. The enclosure includes parallel, spaced apart first and second walls and a slot between them and open to a peripheral edge of the enclosure. First and second longitudinally aligned openings are formed in the first and second walls, respectively. A generally planar locking plate having a central aperture formed therethrough is supported in the slot. The locking plate reciprocates between an open position in which the central aperture is substantially aligned with the first and second openings, and a locking position wherein a locking blade portion of the plate along said central aperture is located between the first and second openings. A biasing means in the slot urges the locking plate in a locking direction, and stop means limit movement of the plate in the locking direction.

The apparatus further includes a catheter connector integral with the proximal end of a transluminal balloon catheter. The catheter connector is adapted for at least partial longitudinal insertion into the (laser enhanced) fiber optic catheter housing through the first and second openings and central aperture. A central longitudinal bore is formed through the catheter connector for accommodating an optical fiber, and an annular groove is formed in the connector exterior surface. During insertion, the groove is positionable in the slot to receive the locking blade portion, thus to form an interlocking engagement between the fiber optic catheter housing connector and balloon catheter connector.

Another aspect of the present invention is an apparatus for releasably connecting the proximal end of a transluminal balloon catheter with respect to a sheath enclosing an optical fiber. The apparatus includes the catheter connector, and further includes a sheath enclosing at least a portion of the optical fiber. Also, a sheath connector is provided for releasably joining the sheath with respect to the balloon catheter connector. The sheath connector includes an elongate cylindrical body mounted to the distal end of the sheath and having a longitudinal fiber accommodating bore therethrough. A disc extends radially outward from the body, and a sleeve extends distally from the perimeter of the disc and surrounds a portion of the body in coaxial relation thereto. A plurality of elongate, longitudinally directed levers are mounted to the disc perimeter. Each lever has a first section distally of the disc and normally aligned with the sleeve, with a radially inward facing detent at its distal end. The balloon catheter connector has an annular recess in its exterior surface, proximally of the groove, for receiving and retaining the detents when the sheath connector and balloon catheter connector are fully engaged.

The sheath connector preferably includes a plurality of keys extended radially from the body at selected locations distally of the disc. The balloon catheter connector then has a plurality of key receiving slots at corresponding selected locations about the longitudinal bore. The longitudinal bore is of sufficient size to accommodate partial longitudinal insertion of the body, with the keys and slots alignable to permit the longitudinal insertion.

The keys and corresponding slots can have different select locations, corresponding to different matched sets (e.g. with matched lengths or diameters) of balloon catheter manifolds and sheaths. This eliminates any chance of inserting the improper sheath into a manifold. The detents readily slip into the annular recess upon full sheath connector insertion, giving a positive tactile indication that insertion is complete.

To facilitate subsequent connection of the (laser enhanced) fiber optic catheter housing, the locking plate preferably extends outward beyond the peripheral edge of the locking plate enclosure, and includes an angled handle portion. The handle portion facilitates use of the thumb of the hand gripping the housing to move the locking plate to the open position, enabling connection of the housing and balloon catheter manifold. Substantially flat alignment edges in the first and second openings, and a corresponding flat portion of the manifold connector, ensure proper angular alignment of the manifold and housing when joined.

Thus, the connecting apparatus ensures proper connection of the fiber enclosing sheath to the catheter manifold, and subsequent connection of the housing, independently of the sheath. Further, the physician can make the necessary connections with accuracy, devoting a modicum of attention to the connecting apparatus while concentrating mainly on the procedure at hand. The locking plate when in the locking position retains both the housing and sheath connector substantially integrally relative to the manifold connector, ensuring the accurate advancement of the optical fiber within the balloon catheter.

IN THE DRAWINGS

These and other features and advantages of the invention are more clearly understood upon reading the following detailed description in view of the accompanying drawings, in which:

FIG. 2 is a front elevational view of a sheath connector separated from the sheath of FIG. 1;

FIG. 3 is a sectional view taken along the line 3-3 in FIG. 2;

FIG. 4 is a front elevational view of a fiber optic catheter housing connector of the housing of FIG. 1, with a locking blade thereof in a locking position;

FIG. 5 is a view similar to FIG. 4 showing the locking blade in an open position;

DETAILED DESCRIPTION OF THE PREFERRED EMBODIMENT

Figure 1:
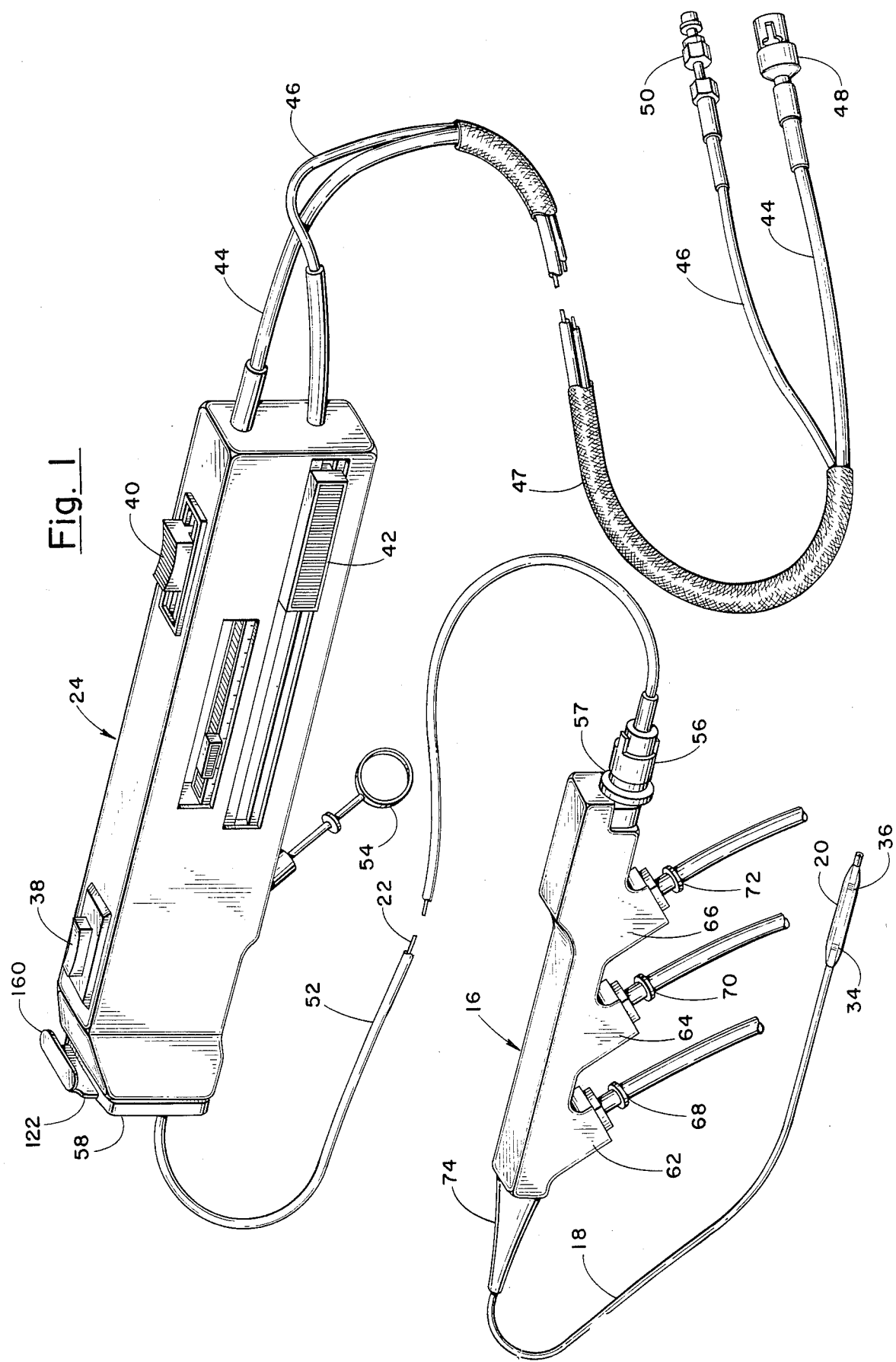
FIG. 1 is perspective view of a (laser enhanced) fiber optic catheter housing, fiber enclosing sheath, and balloon catheter manifold constructed in accordance with the present invention.

Turning now to the drawings, there is shown schematically in FIG. 1 an angioplasty catheter assembly including a balloon catheter manifold 16 and a transluminal angioplasty balloon catheter 18 extended from the distal end of the catheter manifold. At the distal end of the catheter is a balloon 20.

An optical fiber 22 is contained in catheter 18, and runs rearwardly from the catheter through the catheter manifold into a (laser enhanced) optic catheter housing 24, whereby the optical fiber may be advanced or retracted in the balloon catheter. If desired, radiopaque markers are provided near the balloon catheter distal end as shown at 34 and 36, to enable a physician to determine the location of the balloon catheter when it is inserted into a blood vessel.

As seen in the figure, (laser enhanced) fiber optic catheter housing 24 and balloon catheter manifold 16 are separable from one another, which enables a controlled insertion of optical fiber 22 through the manifold and into catheter 18. Provided on the top of housing 24 is a laser actuator switch 38, electrically connected to a power supply, for enabling the transmission of laser energy through optical fiber 22. Rearwardly of switch 38 is a zero adjust slide 40, which comprises a movable member mounted to slide longitudinally with respect to the housing. Also movable slidably in the housing is a fiber advance member 42.

Extended from the rearward end of (laser enhanced) fiber optic catheter housing 24 is an electrical cable 44 through which laser actuator switch 38 and zero adjust slide 40 are electrically linked to the power supply. Adjacent cable 44 is an optical fiber cable 46 which contains a portion of optical fiber 22. A flexible sleeve 47 keeps the cables together. An electrical connector 48 at the proximal end of electric cable 44 is adapted for connection to the power supply, while an optical connector 50 at the proximal end of the optical fiber cable optically links fiber 22 with a laser source.

Between (laser enhanced) fiber optic catheter housing 24 and balloon catheter manifold 16 is an optical fiber sheath 52 which enters the distal end of the fiber advance housing and emerges beneath the housing to a pull ring 54. The sheath is connected to a sheath connector 56 shown against a catheter manifold connector 57 at the proximal end of manifold 16. A housing connector 58, mounted on the distal end of the (laser enhanced) fiber optic housing, lockingly engages balloon catheter manifold connector 57 to connect the (laser enhanced) fiber optic housing to the balloon catheter manifold when desired.

The catheter manifold has first, second and third extensions 62, 64 and 66, to which are connected first, second and third luers 68, 70 and 72. First luer 68 provides fluids to balloon 20 in order to control its inflation and deflation. Second and third luers 70 and 72 deliver treatment fluids, as required, to a central lumen in catheter 18. A conical relief member 74 supports the proximal portion of catheter 18 near the manifold forward end, protecting it against sharp bends.

FIGS. 2 and 3 respectively show sheath connector 56 in front and side section elevation. At the center of connector 56 is an elongate, cylindrical body 76. A central, longitudinal fiber accommodating bore 78 through body 76 surrounds optical fiber 22 and, at the distal or forward end, is somewhat enlarged to house a fiber insertion tube 80 (FIG. 7) extended distally of the sheath connector. Part of the cylindrical body is comprised of a forward end plug 82 inserted into the remainder of the body after the loading of a disc-shaped seal 84. The purpose of seal 84 is to prevent fluids, entering catheter manifold 16 through luers 70 and 72, from flowing backwardly through body 76.

Extended radially outward from body 76 is a support disc 86 which supports at its perimeter a sleeve 88 projecting longitudinally and forwardly of the disc. Also mounted to the disc perimeter are a pair of opposed upper and lower levers 90 and 92. Upper lever 90 has a first section 94 extended forwardly of disc 86, and a second section 96 extended rearwardly or proximally of the disc. At the forward end of lever 90 is a detent 98 directed radially inward of the lever. Lower lever 92 is similarly constructed, with first and second sections 100 and 102 and inwardly directed detent 104. Normally the levers are aligned with sleeve 88, with first sections 94 and 100 in effect forming parts of the sleeve.

Preferably, sheath connector 56 is constructed of an elastically deformable material such as a plastic. This permits levers 90 and 92 to be pivoted, about an axis at the lever/disc junction, to a forward and diverging relation to body 76. This locates detents 98 and 104 farther away from body 76, as compared to their normal position, allowing the release of sheath connector 56 from manifold connector 57 by pinching second sections 96 and 102 toward the body.

For connection with sheath 52 (FIG. 7), the proximal end of body 76 is inserted through a hole 106 in a sheath cap 108 fixed to the sheath by an adhesive 110. A pair of opposed ramp stops 112 and 114, extending radially from body 76, have transverse distal edges which abut an end wall 116 of cap 108, thus to permanently attach sheath connector 56 with respect to sheath 52, yet allow the sheath connector to rotate relative to the sheath.

Forwardly of disc 86, a pair of opposed keys 118 and 120 extend radially from the cylindrical body. The keys can have alternative orientations, for example 90° apart or 135° apart. Various orientations of keys and key slots can ensure proper matching of catheters and fiber sheaths.

As seen from FIGS. 4 and 5, housing connector 58 includes generally planar locking plate 122 and a locking plate enclosure 124 containing the locking plate. The enclosure has parallel and spaced apart first and second walls 126 and 128 with a slot 130 between the walls and open to the top of enclosure 124 to permit the locking plate to extend upwardly out of the enclosure. Formed through first wall 126 is a first opening 132, which is substantially circular except for a flat alignment edge 134 at the top. A second, similar opening is formed in second wall 128, longitudinally aligned with first opening 132 and hence not visible in FIGS. 5 and 6. A central aperture 136 is formed through locking plate 122.

Locking plate 122 is mounted to reciprocate in enclosure 124 between an open position shown in FIG. 5, in which central aperture 136 is substantially aligned with the first and second openings of enclosure 124, and a locking position in which a locking blade portion 138 of plate 122 is positioned between the first and second openings as shown in FIG. 4.

First and second coil springs 140 and 142 are provided inside enclosure 124 near its bottom, and are under compression between locking plate 122 and the enclosure, to urge the locking plate upwardly in a locking direction. First and second opposed portions 144 and 146 of plate 122 are cut away and bent out of the plane of the locking plate (FIG. 7), and abut second wall 128 to retain the locking plate in the enclosure. Hence, the locking blade may be pressed from outside of the enclosure into the open position for connection with or release from manifold connector 57. When released, the locking lever moves to the locking position under the force of springs 140 and 142. The use of only one portion, such as either of portions 144 and 146, has been found satisfactory.

Figure 6:
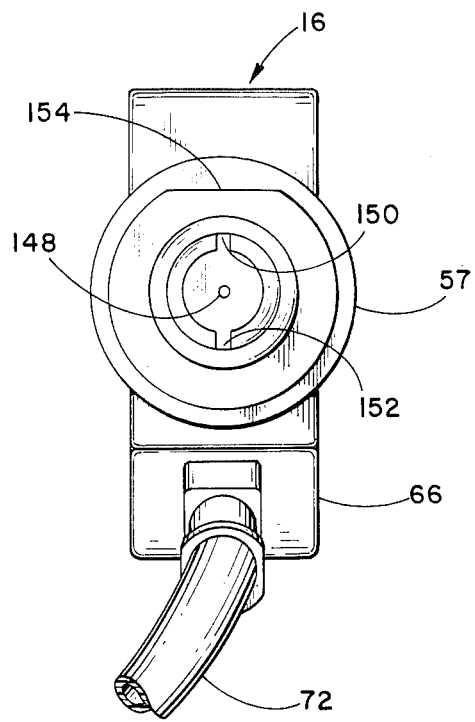
FIG. 6 is a rear elevational view of the balloon catheter manifold and a manifold connector.

FIG. 6 shows manifold connector 57 and the rearward end of catheter manifold 16. An internal longitudinal bore 148 is formed through the manifold connector to accommodate optical fiber 22 and fiber insertion tube 80, and further is sufficiently large to accommodate partial longitudinal insertion of the distal portion of cylindrical body 76. Opposite key receiving slots 150 and 152, formed at the perimeter of bore 148, ensure that only sheath connectors having opposite keys such as keys 118 and 120 can be inserted into the bore. Balloon catheter manifold connector 57 is essentially circular in cross-section, but includes a flat edge 154 formed in its exterior surface and adapted for a facing engagement with alignment edge 134, angularly align catheter manifold 16 and fiber advance housing 24 as they are connected.

Figure 7:
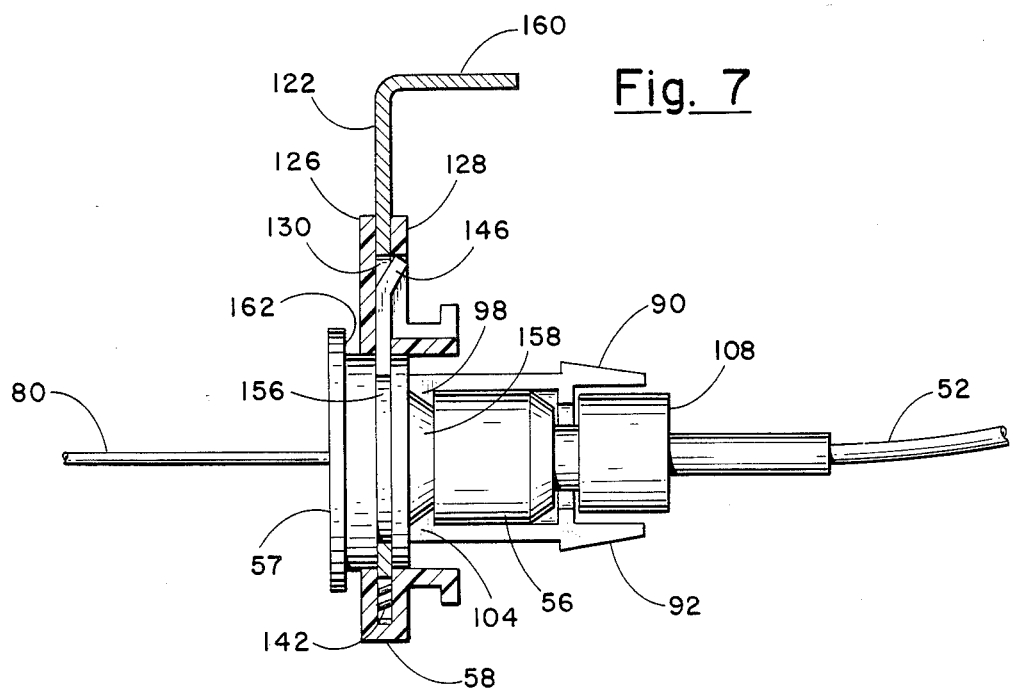
FIG. 7 is a sectional side elevation of the balloon catheter manifold, sheath and housing connectors when joined.

Further details of the manifold connector structure are revealed in FIG. 7. An annular groove 156 is formed in the exterior of the manifold connector and lies parallel to a transverse plane. Also formed in the connector exterior, and rearwardly of groove 156, is an annular recess 158 inclined to accommodate detents 98 and 104.

Usually, (laser enhanced) fiber optic catheter housing 24 and sheath 52 are disconnected from balloon catheter manifold 16 in the early stages of an angioplasty procedure. Then, during procedure, the sheath connector is joined to balloon catheter manifold connector 57, the sheath is drawn rearwardly through the (laser enhanced) fiber optic catheter housing to bring the housing next to the balloon catheter manifold, and finally the housing connector and balloon catheter manifold connector are joined, thus creating the connector configuration shown in FIG. 7.

Sheath connector 56 and manifold connector 57 are joined simply by moving the sheath connector distally relative to the manifold connector, i.e. to the left as viewed in FIG. 7, with the sheath and manifold connectors angularly aligned as determined by the keys and slots. A mismatch of sheath and manifold connectors is impossible since the keys and slots would not align. Levers 90 and 92 flex somewhat as detents 98 and 104 ride along the manifold connector exterior during insertion, and entry of the detents into recess 158 gives a positive, tactile indication that insertion of the sheath connector is complete. While ensuring a correct match of sheath and manifold connectors, the keys and slots require their angular alignment. Such alignment is facilitated because sheath connector 56 is mounted to rotate with respect to sheath 52, and further because annular recess 158 does not constrain detents 98 and 104 to any particular angular orientation against manifold connector 57. One or more markers can be provided on the connectors as a visual aid in their initial alignment.

With connectors 56 and 57 joined, sheath 52 is drawn rearwardly through (laser enhanced) fiber optic catheter housing 24, to move the housing along the sheath until housing connector 58 is positioned for engagement with manifold connector 57. To complete the connection, locking plate 122 is moved to its open position against the force of springs 140 and 142. A physician or other operator accomplishes this by pressing downward upon an angled handle portion 160 integral with the locking plate, typically using the thumb of the hand which grips the fiber advance housing. Then, the fiber advance housing is moved forward until first wall 126 of the housing connector abuts a distal wall 162 of the manifold connector. Handle portion 160 is released to permit the locking plate to return to the locking position under the force of the springs. The alignment edges of the first and second openings, and the corresponding flat edge of manifold connector 57, cooperate to align the housing and manifold connectors during insertion.

Thus, the catheter manifold/sheath connection and the manifold/housing connection can be made rapidly and accurately. The associated keys and slots eliminate the risk of connecting the wrong sheath, and the annular recess and detents cooperate to firmly secure the sheath connector. With the housing and manifold connectors joined, locking blade portion 138 is firmly nested within annular groove 156 to substantially integrally link the catheter manifold and fiber advance housing. In short, the connectors facilitate joinder of the sheath and fiber advance housing to the catheter manifold, while requiring minimal attention from the physician.

What is claimed is:

1. Apparatus for releasably connecting the proximal end of a transluminal catheter with respect to a housing, including:
    a locking plate enclosure mounted at the distal end of a housing and including parallel, spaced apart first and second walls forming a slot therebetween open to a peripheral edge of the enclosure, and first and second longitudinally aligned openings formed in the first and second walls, respectively; a generally planar locking plate having a central aperture formed therethrough and supported in said slot to reciprocate between an open position wherein said central aperture is substantially longitudinally aligned with said first and second openings, and a locking position wherein a locking blade portion of said locking plate along said central aperture is located between said first and second openings; a biasing means in said enclosure for urging the locking plate in a locking direction; and a stop means for limiting movement of the locking plate in said locking direction; and
    a transluminal catheter including a catheter connector integral with the proximal end of the catheter, and adapted for at least partial longitudinal insertion into said housing through said first and second openings and central aperture, said catheter connector having a central longitudinal bore therethrough for accommodating an optical fiber, and further having an annular groove formed in its exterior surface; said groove, during said insertion, positionable in said slot to receive said locking blade portion, thus to form an interlocking engagement between said locking plate and said catheter connector.

2. The apparatus of claim 1 wherein:
    said first and second openings are substantially circular except for an alignment edge formed along at least one of said openings, and wherein a corresponding edge is formed in the exterior surface of said catheter connector and positioned for a facing engagement with said alignment edge during said interlocking engagement, thereby to determine the angular alignment of said housing and said catheter connector.

3. The apparatus of claim 1 wherein:
    said locking plate includes an outer end portion extended transversely beyond said peripheral edge of the enclosure, said outer end portion including an angled handle portion.

4. The apparatus of claim 1 wherein:
    said biasing means comprises a plurality of coil springs under compression between said enclosure and said locking plate; and said stop means includes at least one portion of said locking plate bent away from the plane of the locking plate a sufficient degree to encounter at least one of said first and second walls, thereby to prevent further locking plate movement in the locking direction.

5. The apparatus of claim 1 further including:
    a sheath running through said first and second openings and said central aperture, movable with respect to the housing, and enclosing a portion of the optical fiber;
    a sheath connector for releasably joining said sheath with respect to said catheter connector, including an elongate cylindrical body mounted to a distal end of said sheath and having a longitudinal fiber accommodating bore therethrough; a disc extended radially outward from the body; a sleeve extended distally from the perimeter of the disc and surrounding a portion of said body in coaxial relation thereto; and a plurality of elongate, longitudinally directed levers mounted to said disc perimeter, with at least a section of each lever extending distally of the disc and normally aligned with said sleeve, and a radially inward facing detent at a distal end of each lever;
    wherein said catheter connector has an annular recess in its exterior surface, proximally of said groove, for receiving and retaining said detents when said sheath connector and catheter connector are fully engaged.

6. The apparatus of claim 5 wherein:
    said sheath connector further includes a plurality of keys extended transversely from said body at selected locations distally of said disc; and said catheter connector includes a plurality of key receiving slots formed at corresponding selected locations about said longitudinal bore, said longitudinal bore being of sufficient size to accommodate at least partial longitudinal insertion of said body, with said keys and slots alignable to allow said longitudinal insertion.

7. The apparatus of claim 6 wherein:
    said keys and slots are selectively located to permit connection of said sheath connector and catheter connector only when properly matched.

8. The apparatus of claim 5 including:
    a cap fixed to the distal end of said sheath and having an end wall with a hole therethrough for receiving said body, and a plurality of retainers fixed to said body proximally of said disc, each of said retainers having a radially directed distal edge adapted to contact said end wall, to secure said sheath connector with respect to said sheath.

9. The apparatus of claim 5 including:
    a seal provided in said fiber accommodating bore through said body, for preventing back-flow of fluids in said bore.

10. The apparatus of claim 5 wherein:
    said levers and disc are elastically deformable to permit the pivoting of said levers to a forwardly diverging relation to said body, for withdrawing said detents from said annular recess.

11. The apparatus of claim 10 wherein:
    each lever further includes a section proximal to said disc, and said forwardly diverging relation is achieved by moving said proximal sections toward said body.

12. The apparatus of claim 1 wherein:
said catheter is a balloon catheter, and said housing is a laser enhanced fiber optic catheter housing.

13. Apparatus for releasably connecting the proximal end of a transluminal catheter with respect to a sheath enclosing an optical fiber, including:
a transluminal catheter including a catheter connector integral with the proximal end of the catheter, said catheter connector having a central longitudinal bore therethrough for accommodating an optical fiber, and further having an annular recess formed in its exterior surface;
a sheath enclosing at least a portion of said optical fiber, and a sheath connector for releasably joining said sheath with respect to said catheter connector, including an elongate cylindrical body mounted to a distal end of said sheath and having a longitudinal fiber accommodating bore therethrough; a disc extended radially outward from the body; a sleeve extended distally from the perimeter of the disc and surrounding a portion of said body in coaxial relation thereto; and a plurality of elongate, longitudinally directed levers mounted to the disc perimeter, at least a section of each lever extending distally of the disc and normally aligned with said sleeve, with a radially inward facing detent at a distal end of each lever;
an angular groove in said catheter connector positioned for receiving and retaining each of said detents when said sheath connector and catheter connector are fully engaged.

14. The apparatus of claim 13 wherein:
said sheath connector further includes a plurality of keys extended transversely from said body at selected locations distally of said disc; and said catheter connector includes a plurality of key receiving slots at corresponding selected locations about said longitudinal bore; said longitudinal bore being of sufficient size to accommodate longitudinal insertion of said body, with said keys and slots alignable to permit said longitudinal insertion.

15. The apparatus of claim 13 including:
a cap fixed to the distal end of said sheath and having an end wall with a hole therethrough for receiving said body, and a plurality of retainers fixed to said body proximally of said disc, each of said retainers having a radially directly distal edge adapted to contact said end wall, to secure said sheath connector with respect to said sheath.

16. The apparatus of claim 13 including:
a seal provided in said central longitudinal bore through said body, for preventing backflow of fluids therethrough.

17. The apparatus of claim 13 wherein:
said levers and disc are elastically deformable to permit a pivoting of said levers to a forwardly diverging relation to said body, for withdrawing said detents from said annular recess.

18. The apparatus of claim 17 wherein:
each lever further includes a section proximal to said disc, and said forwardly diverging relation is achieved by moving said proximal sections toward said body.

* * * * *